United States Patent
Furtaw et al.

(10) Patent No.: US 8,154,714 B2
(45) Date of Patent: Apr. 10, 2012

(54) GAS ANALYZER

(75) Inventors: Michael D. Furtaw, Lincoln, NE (US);
Robert D. Eckles, Malcolm, NE (US);
Georgiy G. Burba, Lincoln, NE (US);
Dayle K. McDermitt, Lincoln, NE (US);
Jonathan M. Welles, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 227 days.

(21) Appl. No.: 12/266,379

(22) Filed: Nov. 6, 2008

(65) Prior Publication Data
US 2010/0110437 A1    May 6, 2010

(51) Int. Cl.
*G01N 21/00* (2006.01)

(52) U.S. Cl. .......................................... 356/72

(58) Field of Classification Search ............... 356/437, 356/72–73; 73/31.05, 31.04; 374/143, E13.001
See application file for complete search history.

(56) References Cited

U.S. PATENT DOCUMENTS

| | | | |
|---|---|---|---|
| 4,288,062 A * | 9/1981 | Gupta et al. ............... | 266/88 |
| 6,317,212 B1 | 11/2001 | Eckles | |
| 6,369,387 B1 | 4/2002 | Eckles | |
| 6,722,193 B1 | 4/2004 | Conway | |
| 2001/0045521 A1 | 11/2001 | Prozzo et al. | |
| 2001/0048079 A1 | 12/2001 | Brunamoti et al. | |
| 2008/0032347 A1 | 2/2008 | Sarofim et al. | |
| 2010/0110438 A1 | 5/2010 | Furtaw et al. | |

FOREIGN PATENT DOCUMENTS

| | | |
|---|---|---|
| JP | 8-273939 A | 10/1996 |
| JP | 11-307705 A | 11/1999 |
| JP | 11304705 A | 11/1999 |
| KR | 10-2006-0050193 A | 5/2006 |

OTHER PUBLICATIONS

Burba et al., "Combining the Strengths of Open-Path and Closed-Path Designs into a Single CO2/H2O Gas Analyzer," American Geophysical Union Fall Meeting, San Francisco, California, Dec. 14-18, 2009.

Burba et al., "Eddy Covariance Fluxes of Carbon Dioxide and Water Measured With New Compact Gas Analyzer," 2nd Integrated Land Ecosystem-Atmosphere Processes Study Science Conference, Melbourne, Australia, Aug. 24-28, 2009.

Burba et al., "Eddy Covariance Measurements of CO2 and H2O Fluxes With New Compact Gas Analyzer," 10th International Congress of Ecology, Brisbane, Australia, Aug. 16-21, 2009.

(Continued)

*Primary Examiner* — Tarifur Chowdhury
*Assistant Examiner* — Abdullahi Nur
(74) *Attorney, Agent, or Firm* — Kilpatrick Townsend & Stockton LLP; Gerald T. Gray

(57) ABSTRACT

Gas analyzer systems and methods for measuring concentrations of gasses and in particular dry mole fraction of components of a gas. The systems and method allow for rapid measurement of the gas density and/or dry mole fraction of gases for a number of environmental monitoring applications, including high speed flux measurements. A novel coupling design allows for tool-free removal of a cell enclosing a flow path to enable in field cleaning of optical components.

41 Claims, 4 Drawing Sheets

OTHER PUBLICATIONS

Burba et al., "Measurements of CO2 and H2O Fluxes with New Enclosed Design and with Modified Open-path Design of Fast Gas Analyzers," European Geosciences Union General Assembly, Vienna, Austria, May 2-7, 2010.

Burba et al., "Measurements of Evapotranspiration and Carbon Dioxide Exchange Using New Compact Closed-Path Gas Analyzer and Eddy Covariance Technique," The 2009 International Annual Meetings of the ASA, CSSA, and SSSA. Pittsburgh, Pennsylvania, Nov. 1-5, 2009.

Burba et al., "New Compact Gas Analyzer for Eddy Covariance Measurements of Carbon Dioxide and Water Vapor Fluxes," 15th WMO/IAEA Meeting of Experts on Carbon Dioxide, Other Greenhouse Gases, and Related Tracer Measurement Techniques. Max-Planck-Institute for Biogeochemistry, Jena, Germany, Sep. 7-10, 2009.

Burba et al, "New CO2/H2O Gas Analyzer Combines The Advantages of Open-Path and Closed-Path Solutions," AsiaFlux—2009, Integrating Cross-scale Ecosystem Knowledge: Bridges and Barriers. Hokkaido University, Sapporo, Japan, Oct. 27-29, 2009.

Burba et al., Poster presentation "Small Closed-Path CO2—H2O Gas Analyzer for Eddy Covariance Measurements.," The 8th International Carbon Dioxide Conference. Max-Planck-Institute for Biogeochemistry, Jena, Germany, Sep. 13-19, 2009.

Burba et al., "New $CO_2$ and $H_2O$ Gas Analyzer Design Combines Open-Path and Closed-Path Advantages," 2009 AmeriFlux Principal Investigator Workshop, DOE, Washington DC, Sep. 21-23, 2009.

Burba et al., "New CO2/H2O Gas Analyzer for Eddy Covariance Flux Measurements," 94th Ecological Society of America Annual Meeting, Albuquerque, New Mexico, Aug. 2-7, 2009.

Burba et al., Novel Design of an Enclosed $CO_2/H_2O$ Gas Analyze For Eddy Covariance Flux Measurements, *Tellus*, p. 1-6, Jun. 10, Aug. 1-6, 2010.

Burba et al., "Two New Low-Power and Light-Weight Solutions for Fast Measurements of $CO_2$ and $H_2O$ Ecosystem Exchange," 95th Annual Meeting of Ecological Society of America, Pittsburgh, Pennsylvania, 2010.

PCT Search Report and Written Opinion of Jun. 30, 2009 for application PCT/US2008/082671.

Leuning et al., "The Relative Merits of Open- and Closed-Path Analysers for Measurement of Eddy Fluxes," Global Change Biology (1996) 2, 241-253. Blackwell Science Ltd.

Suyker et al., "Eddy Correlation Measurement of $CO_2$ Flux Using a Closed-Path Sensor: Theory and Field Tests Against an Open-Path Sensor," Boundary-Layer Meteorology 64: (1993) 391-407. Kluwer Academic Publishers, The Netherlands.

Leuning et al., "Comparison of Eddy-Covariance Measurements of $CO_2$ Fluxes by Open- and Closed-Path $CO_2$ Analysers," Boundary-Layer Meteorology 59: (1992) 297-311. Kluwer Academic Publishers, The Netherlands.

Burba et al., "Addressing the Influence of Instrument Surface Heat Exchange on the Measurements of $CO_2$ Flux From Open-Path Gas Analyzers," Global Change Biology, 14: (2008) 1854-1876. Blackwell Publishing Ltd.

* cited by examiner

BLOCK DIAGRAM OF A PRESSURE MEASUREMENT SCHEME

The top image is a typical metal sample cell, while the lower image shows an insulated cell where the only heat flux comes from the windows on either end. In both cases, the error is calculated by the actual temperature minus an un-weighted average of the inlet and outlet temperatures.

BLOCK DIAGRAM OF SAMPLE CELL. THE INLET TEMPERATURE IS MEASURED AT 'A', THE PRESSURE IS MEASURED AT 'B', THE OUTLET TEMPERATURE IS MEASURED AT 'C', AND THE GAS CONCENTRATIONS ARE A VOLUME-AVERAGED MEASUREMENT CONTAINED WITHIN THE DOTTED OUTLINE

GAS ANALYZER

BACKGROUND

The present invention relates generally to gas analysis, and more particularly to systems and methods for measuring concentrations of gases.

The increasing carbon dioxide concentration in the atmosphere and the resulting greenhouse effect and climate change have become important topics for scientific research. In order to understand the global carbon balance, it is necessary to determine the rate at which carbon dioxide and energy exchanges between the atmosphere and terrestrial and oceanic ecosystems. A measurement technique called "eddy covariance" has been widely used to determine these rates. The air within a few hundred meters above the earth surface is mostly turbulent, so that turbulent structures (vortices of variable sizes) called "eddies" are responsible for the vertical transport of the most of the gases, including carbon dioxide and water vapor, and also heat and momentum between the surface and the atmosphere. The rates of such transport can be calculated from simultaneous, high-frequency measurements of the vertical component of wind speed, the concentrations of carbon dioxide and water vapor, and the air temperature.

To measure concentrations of carbon dioxide and water vapor, a gas analyzer can be used to analyze the transmittance of light in appropriate wavelength bands through a gas sample. With some gas analyzers, a sample gas containing unknown gas concentrations of carbon dioxide and water vapor is placed in a sample cell, and a reference gas with zero or known concentrations of carbon dioxide and water vapor is placed in a reference cell. The analyzer measures the unknown gas concentrations in the sample cell from calibrated signals that are proportional to the difference between light transmitted through the sample cell and light transmitted through the reference cell.

In eddy covariance applications, ambient air that is full of dust and pollen must be moved through the analyzer at high flow rates in order for the analyzer to have the necessary frequency response. Even when the air is filtered, contamination of the sample cells is to be expected especially during long deployments, requiring the analyzer to be returned to the factory for cleaning. This is an expensive and time-consuming process, especially when the analyzer is used in a remote location such as the Amazon basin, the north slope of Alaska, or the deserts of Africa.

There is a need, therefore, for an improved gas analyzer. In particular, there is a need for gas analyzers that are easy to clean and that provide robust measurement capabilities.

BRIEF SUMMARY

Systems and methods are provided for measuring concentrations of gases and in particular dry mole fraction of components of a gas. The systems and method according to various embodiments allow for rapid measurement of the gas density and/or dry mole fraction of gases for a number of environmental monitoring applications, including high speed flux measurements.

According to various embodiments, systems and methods are provided that enable rapid measurements of gas concentrations simultaneously with rapid measurements of pressure and temperature of sampled gas. In addition, devices according to various embodiments can advantageously use substantially shorter intake tubes as compared to previously existing devices, and substantially lower power consumption.

Various embodiments also provide unique mechanical-optical design solutions for a gas analyzer that include several novel elements in a tool-free removable gas cell. Various embodiments also allow for measuring the dry mole fraction of a gas in a removable gas cell using temperature and pressure measurement in the gas stream.

According to one aspect of the present invention, a gas analyzer is provided that typically includes a detector section including a detector, a source section including a light source, and a removable gas cell removably disposed between the source and detector sections. The removable gas cell typically includes a housing structure defining a gas flow channel, e.g., an enclosed gas flow channel, wherein, when attached, emitted light from the light source passes through the gas flow channel to the detector section along a light path. The gas cell also typically includes a gas inlet port, a gas outlet port, wherein the inlet and outlet ports are located on the housing structure, and a first temperature sensor adapted to measure a temperature of gas flowing in the flow channel, and a pressure sensor located at an interior point of the housing structure in the gas flow channel, the pressure sensor adapted to measure a pressure of the gas at an interior point in the flow cell. In certain aspects, the removable gas cell further includes a second temperature sensor located proximal to the outlet port, wherein the first temperature sensor is located proximal to the input port.

According to another aspect of the present invention, a gas analyzer is provided that typically includes a detector section including a detector, a source section including a light source, and a removable gas cell removably disposed between the source and detector sections. The removable gas cell typically includes a housing structure defining a gas flow channel, e.g., an enclosed gas flow channel, wherein, when attached, emitted light from the light source passes through the gas flow channel to the detector section along a light path. The gas cell also typically includes a gas inlet port, a gas outlet port, wherein the inlet and outlet ports are located on the housing structure, and a first temperature sensor located proximal to the inlet port, and a second temperature sensor located proximal to the outlet port. In certain aspects, the gas analyzer includes a pressure sensor located at an interior point of the housing structure in the gas flow channel, the pressure sensor adapted to measure a pressure of the gas at an interior point in the flow cell.

In certain aspects, the gas analyzers include an intelligence module coupled with the temperature sensor(s), with the pressure sensor and with the detector. The intelligence module is typically adapted to determine a dry mole fraction of components of a gas within the flow channel based on a detector signal and substantially simultaneous measurements of the pressure of the gas by the pressure sensor and the temperature of the gas by the temperature sensor(s). In certain aspects, the intelligence module corrects for a delay due to spatial separation in the temperature signals received from the first and second temperature sensors, wherein the delay is typically a function of a flow rate of the gas in the flow channel. In certain aspects, the gas analyzers include a first optical window proximal to the detector section and a second optical window proximal to the source section, wherein the first and second optical windows provide an airtight seal for components within the source and detector sections.

According to yet another aspect of the present invention, a method is provided for measuring dry mole fraction of components of a gas in a flow cell of a gas analyzer. The method typically includes flowing a gas through the flow cell, measuring an absorbance of light of the components of the gas in the flow cell, substantially simultaneously measuring a temperature, T1, of the gas at an input port of the flow cell, substantially simultaneously measuring a temperature, T2, of the gas at an output of the flow cell, and substantially simultaneously measuring a pressure, P, of the gas at an interior point of the flow cell. The method also typically includes determining a dry mole fraction of the components of the gas based on the measured absorbance, P, T1 and T2. In certain aspects, the components of the gas include $CO_2$ and $H_2O$, and wherein the gas is air.

According to yet a further aspect, a gas analysis system that measures dry mole fraction of components of a gas is provided. The system typically includes a flow cell within which a gas is flowed from an inlet port to an outlet port, a light source configured to transmit light through the flow cell, and a detector subsystem configured to output an absorbance signal representing an absorbance of light by the components of the gas in the flow cell. The system also typically includes a first temperature sensor positioned proximal to the input port of the flow cell, a second temperature sensor positioned proximal to the output port of the flow cell, and a pressure sensor adapted to measure pressure at an interior point of the flow cell. the system further typically includes an intelligence module coupled with the first and second temperature sensors, the pressure sensor, and with the detector subsystem. The intelligence module is typically adapted to determine a dry mole fraction of the components based on the absorbance signal and the substantially simultaneous measurements of the pressure of the gas and of the temperature of the gas by the first and second temperature sensors. In certain aspects, the measurements of the pressure and of the temperature of the gas by the first and second temperature sensors occur within about 0.2 seconds or less of each other. In certain aspects, the measurements of the pressure and of the temperature of the gas by the pressure sensor, and the first and second temperature sensors are taken at a rate of about 1.0 Hz or faster.

According to another aspect, a removable gas cell adapted to be disposed between light source and detector sections of a gas analyzer system is provided. The removable gas cell typically includes a housing structure defining a gas flow channel, a first opening at one end of the gas flow channel, a second opening at the other end of the gas flow channel, wherein the first and second openings define a light path along which light from a light source passes through the cell to the detector section. The gas cell also typically includes a gas inlet port, a gas outlet port, wherein the inlet and outlet ports are located on the housing structure off of the optical axis, a first temperature sensor located proximal to the inlet port, and a second temperature sensor located proximal to the outlet port. In certain aspects, the gas cell includes a pressure sensor located at an interior point of the housing structure in the gas flow channel, the pressure sensor adapted to measure a pressure of a gas at an interior point in the flow cell. In certain aspects, at least one of the first and second temperature sensors includes a thermocouple positioned at a central point of a flow path defined by the respective port.

According to still another aspect, a removable gas cell adapted to be disposed between light source and detector sections of a gas analyzer system is provided. The removable gas cell typically includes a housing structure defining a gas flow channel, a first opening at one end of the gas flow channel, a second opening at the other end of the gas flow channel, wherein the first and second openings define a light path along which light from a light source passes through the cell to the detector section. The gas cell also typically includes a gas inlet port, a gas outlet port, wherein the inlet and outlet ports are located on the housing structure off of the optical axis, a first temperature sensor adapted to measure a temperature of a gas flowing in the flow channel, and a pressure sensor adapted to measure a pressure of the gas at an interior point in the flow cell.

In certain aspects, the removable gas cells include, or can be coupled with, a gas intake tube that couples the atmosphere with the input port. The intake tube can advantageously have a length of less than 2.0 meters and more advantageously less than about 1.0 meters.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION

Figure 1:
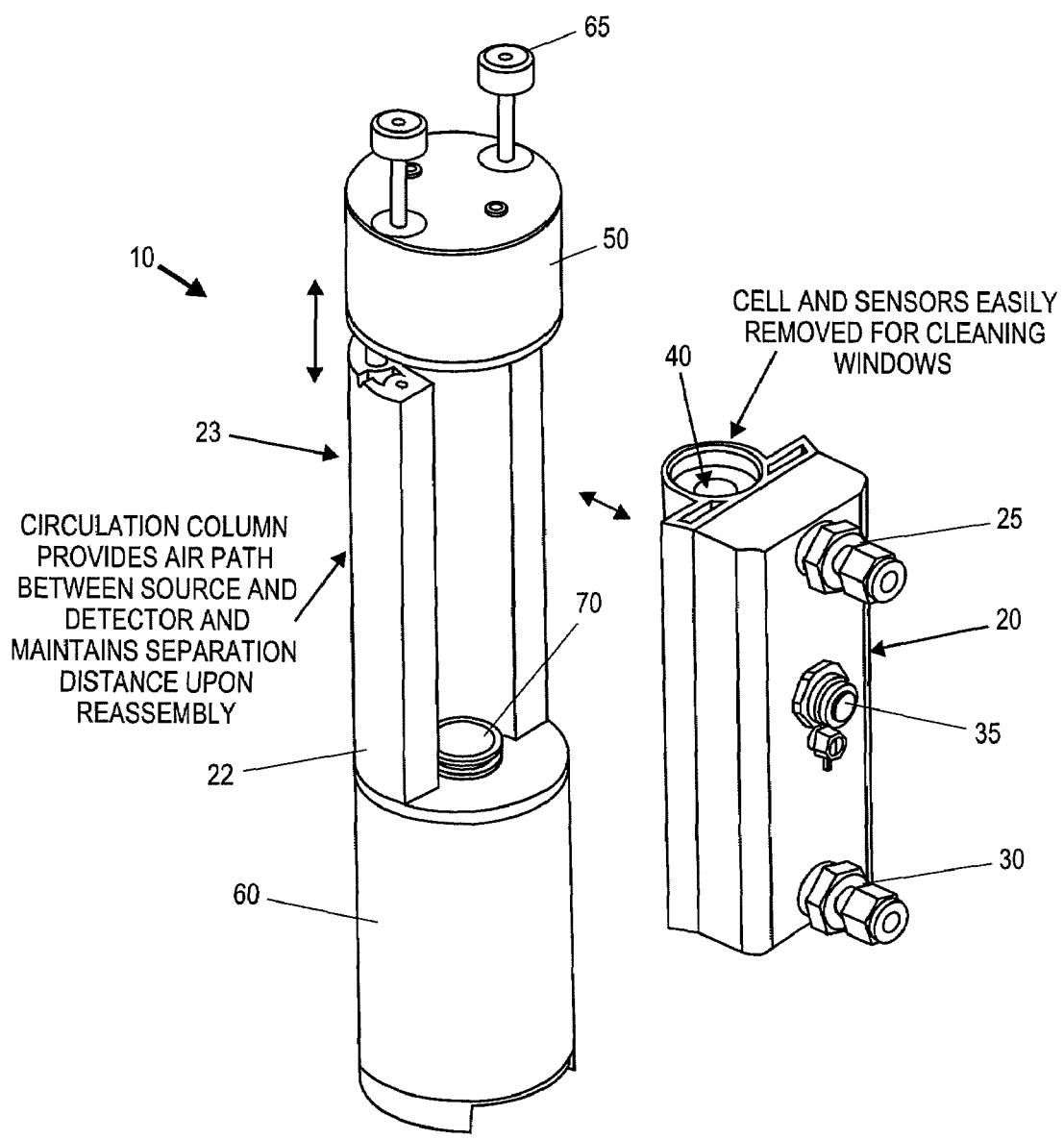
FIG. 1 illustrates a gas analyzer including a removable sample flow cell according to one embodiment.

The present invention provides systems and methods for measuring densities of gasses such as carbon dioxide and water vapor. The systems and methods are particularly useful in turbulent air structures. For example, in certain embodiments, the systems and methods advantageously sample and measure gas concentration, temperature and pressure at high speed and at high bandwidth, and allow for calculation of dry mole fraction of gas components.

Operational Overview

The gas analyzers according to various embodiments generally include a light source, a sample cell, and a detector. The sample cell is removable in certain aspects to facilitate in-field cleaning and repair. The gas analyzers disclosed herein can be used to measure a concentration of one or more gases that have a high absorbance at different wavelength bands. For example, in one application, a gas analyzer can be used to measure a concentration of $CO_2$ and water vapor ($H_2O$) in a sample gas, typically air. Generally, the gas analyzer uses non-dispersive infrared (NDIR) absorption to measure concentration of a gas in a sample cell based on the difference between absorption of infrared radiation passing through the sample cell and a reference cell, or against a calibrated reference signal. Advantageously, the gas analyzers do not require long intake tubes and are capable of taking high speed measurements which enable, inter alia, calculation of dry mole fraction of gas components.

In operation, a light source transmits light having a spectrum of wavelengths through sample and reference cells. Gases present in the sample cell absorb light at different wavelength bands. For example, $CO_2$ has a high absorbance at 4.255 µm, and water vapor has a high absorbance at 2.595 µm. Light exiting the sample cell is detected by the detector, which is sensitive to wavelength bands absorbed by the gases (e.g., $CO_2$ and $H_2O$), or two detectors can be used, each sensitive to the wavelength band absorbed by one of the gases. The concentration of the gases in the sample cell can be determined by calculating the difference between absorption in the sample cell and the reference cell or a reference signal. For example, when a reference cell contains a non-absorber gas, the signal detected in the sample cell is compared to the signal detected in the reference cell to provide an absolute measurement of gas concentration in the sample cell. U.S. Pat. Nos. 6,317,212 and 6,369,387, which are each hereby incorporated by reference in its entirety, disclose various features of open and closed path gas analyzers, including optical filter configurations and techniques.

As described above, contamination of the gas analyzer can result in inaccurate concentration measurements. Contamination can occur in the sample cell and can occur in the sections of the gas analyzer that house the light source and detectors. Additionally, inaccurate concentration measurements can result due to fluctuations in gas temperature. The following embodiments offer solutions to these problems. It should be noted that any of these embodiments can be used alone or in combination with one another.

Removable Flow Cell

According to various embodiments, a gas analyzer includes a packaging scheme that enables simple, tool-free removal of the sample flow cell to facilitate in-field cleaning of optical components such as source and detector optical windows. Such a packaging scheme also advantageously allows for maintaining a desiccant and scrub path (see e.g., U.S. Pat. No. 6,317,212, previously incorporated by reference) and advantageously allows for repeatable set distance between the source and detector.

FIG. 1 illustrates a gas analyzer 10 including a removable sample flow cell 20 according to one embodiment. Sample cell 20 includes a housing structure having a gas inlet port 25 and a gas outlet port 30. A cylindrical portion 40 defines a gas flow path which has two openings at either end. The cylindrical portion may be part of the housing structure of cell 20 or it may itself be separable from the housing structure. In operation, gas enters input port 25, flows through the flow path defined by cylindrical portion 40 and exits outlet port 30. In one embodiment, a pressure sensor 35 (external portion shown) is positioned to measure the pressure at an internal point within the flow path.

Removable sample cell 20 is configured to couple with structure 22 of gas analyzer 10. Structure 22 includes a source portion 60 that houses a light or radiation source and associated electrical and optical components. Structure 22 also includes a detector portion 50 that houses one or more detectors and associated optical and electrical components. A first optical window 70 is provided in one embodiment proximal to source portion 60 as shown in FIG. 1. A second optical window (not shown) is provided in one embodiment proximal to detector portion 50. In typical operation, light (typically IR light) emanating from source portion 60 travels to detector portion 50 along an optical path defined by the first and second optical windows. In one embodiment, an O-ring is provided proximal the first and second optical windows to provide a more robust seal between the sample cell 20 and the housing 22 when in a coupled state.

When in a coupled state, the gas flow path defined by cylindrical portion 40 substantially aligns with the optical path defined by the first and second optical windows. It should be appreciated that the optical path and the flow path do not need to align, and that only a portion of the gas flow path need be contiguous with the optical path. It should also be appreciated that although cylindrical portion 40 includes an open-ended flow path when decoupled from housing 22, optical windows could be coupled to or located on sample cell 20 at either end of the flow path in place of or in addition to the first and second optical windows of structure 22.

In one embodiment, to couple and uncouple sample cell 20 from the gas analyzer housing structure 22, one or more thumbscrews (two shown) are provided to increase or decrease the distance of detector section 50 relative to column 23. When in a coupled state, a user need only activate the thumbscrews, separate detector section 50 a sufficient distance from column 23 and remove sample cell 20. Similarly, to couple sample cell 20 with the gas analyzer, the user would extend the detector section 50 a sufficient distance, insert cell 20 adjacent to column 23 and activate the thumbscrews to re-engage the detector section 50 with column 23 and simultaneously engage sample cell 20 between detector section 50 and source section 60. The optical windows and O-rings help ensure an airtight seal for the gas flow path in sample cell 20. Alternative coupling mechanisms could include a bayonet (such as used in cameras), clamps, clips or other fastening mechanisms.

Advantageously, the design shown in FIG. 1 enables easy removal of the sample cell 20 and associated components. The mechanical packaging scheme enables easy, tool-free removal of the sample cell to clean the source and detector optical windows. This enables use of the gas analyzer (e.g., an IR gas analyzer or IRGA) without need to filter the air sample for dust (which lowers the power requirements for air flow). To maintain air-tight seals and allow the sample cell to be removed, the detector enclosure 50 is extended away from the rest of the assembly as shown in FIG. 1. Air-tight paths are provided from the detector enclosure 50, through circulation column portion 23, to the source enclosure 60 to run $CO_2$ and $H_2O$ free air as well as necessary electrical components. It should be appreciated that the gas analyzer could be configured such that attachment mechanisms enable the source section 60 to extend away from column 23 in addition to or in lieu of detector section 50 extending away from column 23.

Temperature and Pressure Measurements

Knowing the temperature of the sample gas is important for various measurements, such as for calculating the mole fraction from the number density. According to one embodiment, the temperature is measured at the inlet port 25 and at the outlet port 30 of the sample cell 20 in a manner that does not block any of the optical signal (e.g., IRGA signal) in the flow path. The volume average temperature in the cell can be calculated from a relationship between the inlet and outlet temperatures along with the flow rate of the sample gas. In certain aspects, for example, a generic function is $T_{IRGA}=f(T_{in}, T_{out}, T_{block}, U)$, where U is the mean velocity through the cell. In certain aspects, additional temperature sensors may be used, e.g., to measure the block temperature of cylinder 40, and/or to measure the gas temperature at different points in the flow path.

Figure 2:
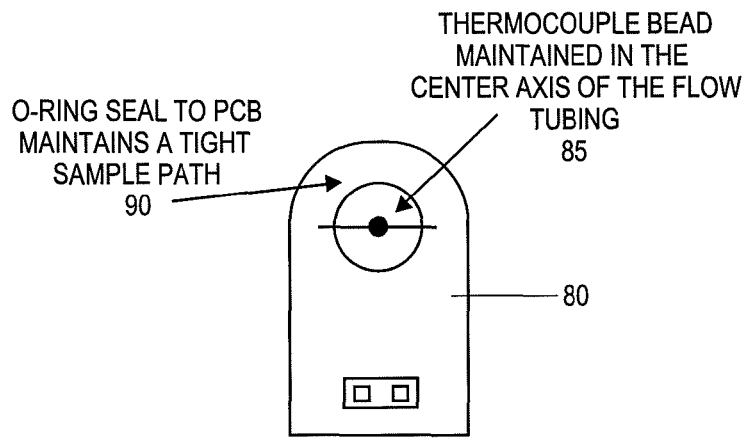
FIG. 2 illustrates a thermocouple design used in the sample cell inlet and outlet according to one embodiment.

In one embodiment, the inlet and outlet temperatures are measured using a disposable thermocouple (e.g., type-E thermocouple). For example, in certain aspects, a thermocouple is strung taught across a printed circuit board with a hole through for the sample gas to flow. FIG. 2 illustrates a thermocouple design used in the sample cell inlet and outlet ports according to one embodiment. A printed circuit board 80 includes an aperture across which is strung a thermocouple bead 85. In certain aspects, the printed circuit board is included in structure 20 or mounted on structure 20 such that the aperture is contiguous with the gas flow path of the entry/exit port 25/30. An O-ring 90 provides an air tight gas path.

This design allows the thermocouples to be easily replaced as well as making sure the temperature measurement is in the center axis of the gas flow. In general it is desirable to obtain accurate measurements with the same frequency response. For example, it is desirable to match the frequency response of the thermocouple to that of the volumetric frequency response, e.g., physical response of the flow cell. For example, a 0.002" thermocouple advantageously provides a frequency response to a 15 liter/minute (LPM) flow that is substantially the same as the signal attenuation due to the volume averaging within the IRGA. In one embodiment, the measurements are synchronized with each other to account for slight timing variations and frequency variations. For example, the measurements of gas concentration (e.g., $CO_2$ and $H_2O$), temperature and pressure are advantageously taken within about 0.2 seconds, and more advantageously within about 0.1 seconds of each other in certain embodiments. this enable a calculation of dry mole fraction as will be described more below. These signals may be aligned in real time to account for time variations/delays as will be discussed more below.

In certain embodiments, a single temperature sensor is used. For example, a single temperature sensor may be located proximal to the inlet port, proximal to the outlet port, or proximal to an internal portion of the flow cell. Temperature measurements can be taken and a volume temperature can be calculated using the single temperature sensor signal and known parameters, such as flow rate, flow cell volume, etc. However, it is appreciated that the use of two (or more) temperature sensors as described above will provide a more robust and accurate temperature for the gas in the flow cell.

Figure 3:
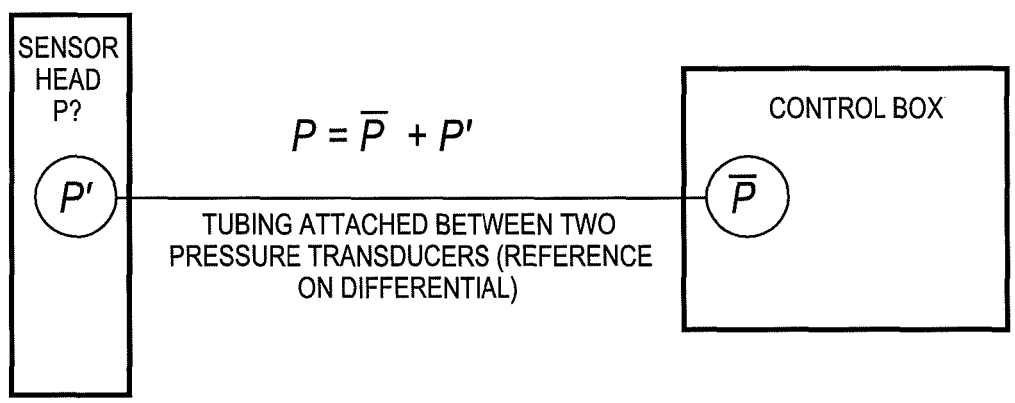
FIG. 3 is a diagram of a pressure measurement scheme according to one embodiment.

It is also important know the pressure in the flow cell to facilitate calculation of mole fraction from number density. FIG. 3 is a diagram of a pressure measurement scheme according to one embodiment. In one embodiment, the pressure sensor, e.g., sensor 35 includes a differential pressure sensor In order to maintain the sensor head as compact as possible, in one embodiment, a coupled set of absolute/differential pressure transducers are used to obtain high frequency pressure data from the sample cell (since pressure sensor that measures absolute sensor may be quite bulky). The pressure of the gas at the interior of the flow cell can be determined by adding the differential pressure and the mean pressure. In one embodiment, the pressure sensor is a high speed pressure sensor. Useful pressure sensors include a piezoresistive silicon differential pressure transducer (e.g., MPX2010DP, Freescale Semiconductor Inc. (Motorola)) and a piezoresistive silicon absolute pressure transducer (MPX4115A, Freescale Semiconductor Inc. (Motorola)). Other pressure sensors as would be apparent to one skilled in the art may be used.

Figure 4:
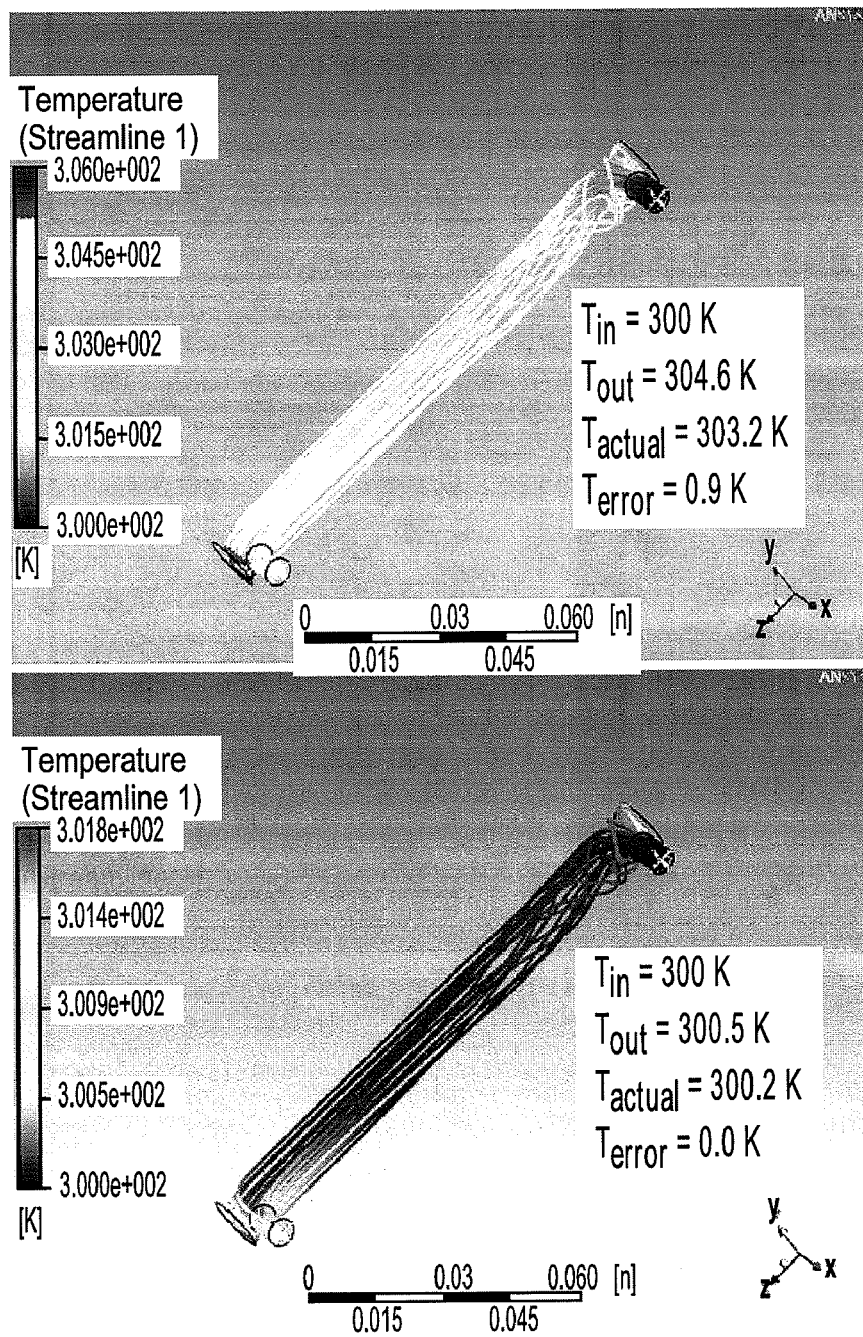
FIG. 4 illustrates thermal conductivity within a flow cell for an un-insulated (top) flow cell and an insulated (bottom) flow cell.

According to one embodiment, the sample flow cell includes an insulating sleeve made out of a low thermal conductivity material and/or pockets of air or vacuum. Useful materials include low-$CO_2$ absorption plastics (e.g., Teflon PTFE (polytetrafluoroethylene) which can be very useful because all plastics absorb some $CO_2$ and water vapor, but Teflon is exceptionally low in absorption) and other suitable materials. A double-wall vacuum metal sleeve or other designs may be used. Such sleeves advantageously minimizes the temperature change between the inlet and outlet thermocouples (to maximize accuracy) by decoupling the air flow from the heat dissipation of the gas analyzer, e.g., heat dissipation due to electronics of gas analyzer. In general, the bigger the temperature change, the more the characterization between the volume average temperature as a function of the two measured temperatures is relied on. Thus, the thermal insulation sleeve, when used, should insulate at least a portion of the flow cell from other components of the system. FIG. 4 illustrates an example of the thermal conductivity within a flow cell for an un-insulated (top) flow cell and an insulated (bottom) flow cell. The top image is a typical metal sample cell, while the lower image shows an insulated cell where the only heat flux comes from the windows on either end. As can be seen, the heat flux is greatly reduced and the error in temperature measurement is also greatly reduced. In both cases, the error is calculated by the actual temperature minus an un-weighted average of the inlet and outlet temperatures.

Figure 5:
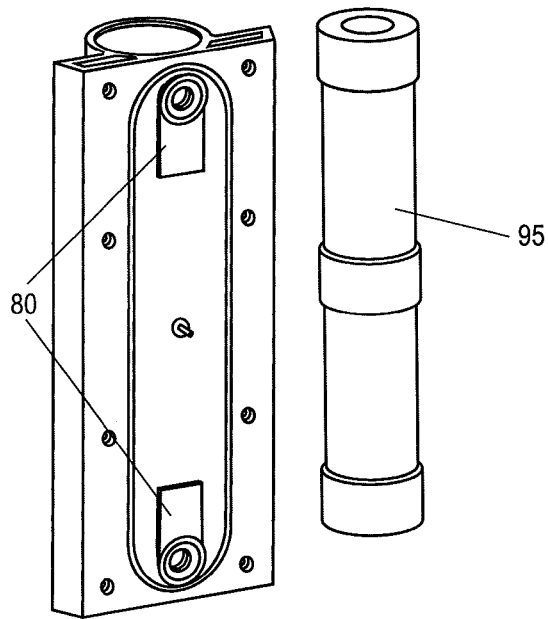
FIG. 5 illustrates one embodiment including a sample cell with a cell insert removed.

FIG. 5 illustrates one embodiment including a sample cell with a cell insert 95 (defining the gas flow path) removed. As can be seen, a position and sealing scheme for the thermocouple boards 80 proximal to both the inlet and outlet ports is also shown.

Mole Fraction Measurement

Figure 6:
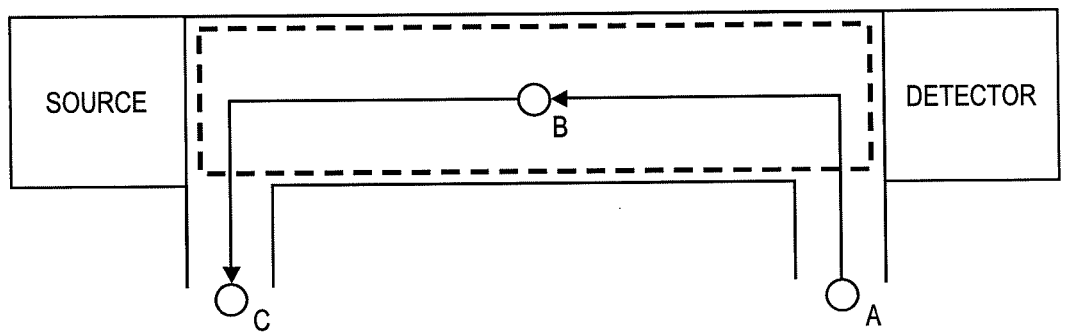
FIG. 6 illustrates a temperature and pressure measurement scheme for a gas flow cell according to one embodiment.

To determine and output mole fraction, calculations should be performed in real time. To implement this, digital electronics receive various signals and perform calculations in real-time. The high speed temperature and pressure signals are acquired from spatially separated sensors. Also, each sensor typically has its own characteristic frequency response (sometimes depending on the flow rate). According to one embodiment, the timing of the sensors is aligned (e.g., delays removed) and the frequency responses, where necessary, are accounted for to calculate the mole fraction in the center of the sample cell (e.g., without directly measuring temperature in that position). As shown in FIG. 6, according to one embodiment, the inlet temperature is measured at point 'A', the pressure is measured at point 'B', the outlet temperature is measured at point 'C', and the gas concentrations are a volume-averaged measurement contained within the dotted outline. In certain aspects, signal alignment occurs in real time as signals are received (e.g., by an intelligence module adapted to process such signals). It should be appreciated, however, that signal processing may be performed later. For example, the signals, or data representing the signals, may be stored and provided to an intelligence module for processing at a later time, after measurements have been taken.

According to one embodiment, the dry mole fraction is determined using a gas analyzer according to the various embodiments disclosed herein. Advantageously, gas analyzers as disclosed herein are capable of making dry mole fraction measurements at high bandwidth. For example, it is desirable to determine a dry mole fraction of $CO_2$ or other gas component at a certain frequency response, e.g., 10 Hz. In order to provide this output, the following steps occur according to one embodiment. First, a flow rate is introduced through the IRGA that purges the volume, for example, at about a 10 Hz or greater purge rate. For example, a flow of ambient air into the inlet port, through the flow cell and out the outlet port is initiated at the desired flow rate. The temperature is then measured at points A and C with a frequency response similar to the volume-average (e.g., type 'E' thermocouples of 0.002" diameter provides a similar response to a flow rate of 15 liters-per-minute (LPM) through the IRGA). The pressure (e.g., differential pressure) is measured at point B with a similar frequency response to the other measurements. The temperature measurements are taken substantially simultaneously with each other and with the pressure measurement. The temperatures at A and C are corrected for spatial separation (e.g., $T_A(t+delay)$ and $T_C(t-delay)$ where the delay is a function of the flow rate and flow path/IRGA geometry). Simultaneously with these measurements, the detector system is determining concentration of gas components (e.g., carbon dioxide and water vapor). In certain aspects, the bandwidth of all the signals (e.g., temperature, pressure, absorbance) is matched to the physical time constant of the flow through the flow cell volume (i.e., flow rate divided by volume). Appendix A illustrates exemplary calculations for determining the dry mole fraction. Once determined, the dry mole fraction may be returned, e.g., displayed or stored for later use.

It should be understood that, herein and elsewhere, when referring to a mole fraction (e.g., $CO_2$ mole fraction) that includes water vapor, the term "mole fraction" is typically used; when referring to a mole fraction after water vapor is removed, the term "dry mole fraction" is typically used, and in certain instances the term "instantaneous mole fraction" or "instantaneous dry mole fraction," may be used to refer to high speed measurements.

It should be appreciated that the gas analysis processes, including the mole fraction determination processes, may be implemented in computer code running on a processor of a computer system. The code includes instructions for controlling a processor to implement various aspects and steps of the gas analysis processes. The code is typically stored on a hard disk, RAM or portable medium such as a CD, DVD, etc. Similarly, the processes may be implemented in a gas analyzer including an intelligence module, typically having one or more processors executing instructions stored in a memory unit coupled to the processor(s). The intelligence module may be part of the gas analyzer, or part of a separate system directly or indirectly coupled with the gas analyzer. Code including such instructions may be downloaded to the gas analyzer memory unit over a network connection or direct connection to a code source or using a portable medium as is well known.

One skilled in the art should appreciate that the processes of the present invention can be coded using a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A gas analyzer, comprising:
   a) a detector section including a detector;
   b) a source section including a light source;
   c) a first optical window coupled with the detector section;
   d) a second optical window coupled with the source section; and
   e) a removable gas cell removably disposed between the source and detector sections, the removable gas cell including:
   a housing structure defining a gas flow channel, wherein the light from the light source passes through the gas flow channel to the detector section along a light path;
   a gas inlet port;
   a gas outlet port, wherein the inlet and outlet ports are located on the housing structure;
   a first temperature sensor adapted to measure a temperature of gas flowing in the flow channel; and
   a pressure sensor located at an interior point of the housing structure in the gas flow channel, the pressure sensor adapted to measure a pressure of the gas at an interior point in the flow cell,
   wherein the first and second optical windows provide an airtight seal for components within the source and detector sections.

2. The gas analyzer of claim 1, wherein the removable gas cell further includes a second temperature sensor located proximal to the outlet port and adapted to measure a temperature of gas within the flow channel proximal to the outlet port, wherein the first temperature sensor is located proximal to the input port.

3. The gas analyzer of claim 1, wherein the pressure sensor is a high speed pressure sensor.

4. The gas analyzer of claim 1, further including a gas intake tube, coupling the atmosphere with the gas input port, the intake tube having a length of less than about 1.0 meters.

5. A gas analyzer, comprising:
   a) a detector section including a detector;
   b) a source section including a light source;
   c) a first optical window coupled with the detector section;
   d) a second optical window coupled with the source section; and
   e) a removable gas cell removably disposed between the source and detector sections, the removable gas cell including:
   a housing structure defining a gas flow channel, wherein the light from the light source passes through the gas flow channel to the detector section along a light path;
   a gas inlet port;
   a gas outlet port, wherein the inlet and outlet ports are located on the housing structure;
   a first temperature sensor located proximal to the inlet port and adapted to measure a temperature of gas within the flow channel proximal to the inlet port; and
   a second temperature sensor located proximal to the outlet port and adapted to measure a temperature of gas within the flow channel proximal to the outlet port,
   wherein the first and second optical windows provide an airtight seal for components within the source and detector sections.

6. The gas analyzer of claim 5, further including a pressure sensor located at an interior point of the housing structure in the gas flow channel, the pressure sensor adapted to measure a pressure of the gas at an interior point in the flow cell.

7. The gas analyzer of claim 6, further including an intelligence module coupled with the first and second temperature sensors, with the pressure sensor and with the detector, the intelligence module adapted to determine a dry mole fraction of components of a gas within the flow channel based on a detector signal and substantially simultaneous measurements of the pressure of the gas by the pressure sensor and the temperature of the gas by the first and second temperature sensors.

8. The gas analyzer of claim 7, wherein the measurements of the pressure and of the temperature of the gas by the first and second temperature sensors occur within about 0.2 seconds or less of each other.

9. The gas analyzer of claim 7, wherein the measurements of the pressure and of the temperature of the gas by the first and second temperature sensors are taken at a rate of about 1.0 Hz or faster.

10. The gas analyzer of claim 7, wherein the intelligence module corrects for a delay due to spatial separation in the temperature signals received from the first and second temperature sensors, wherein the delay is a function of a flow rate of the gas in the flow channel.

11. The gas analyzer of claim 7, wherein the components of the gas include $CO_2$ and $H_2O$, and wherein the gas is air.

12. The gas analyzer of claim 6, wherein the pressure sensor is a high speed pressure sensor.

13. The gas analyzer of claim 5, wherein the removable gas cell further includes a thermal insulation sleeve adapted to thermally insulate at least the housing structure defining the flow channel from components of the gas analyzer.

14. A method of measuring dry mole fraction of components of a gas in a flow cell of a gas analyzer, the method comprising:
   flowing a gas through the flow cell;
   measuring an absorbance of light of a component of the gas in the flow cell;
   substantially simultaneously, and at a rate of about 1.0 Hz or faster:
      i) measuring a temperature, T1, of the gas at an input port of the flow cell;
      ii) substantially simultaneously, measuring a temperature, T2, of the gas at an output of the flow cell; and
      iii) substantially measuring a pressure, P, of the gas at an interior point of the flow cell; and
   thereafter determining a dry mole fraction of the component of the gas based on the measured absorbance, P, T1 and T2.

15. The method of claim 14, wherein determining an absorbance includes comparing a detector signal with a reference signal.

16. The method of claim 14, wherein measuring an absorbance includes:
   transmitting light having a known wavelength band through the flow cell;
   receiving the transmitted light at a detector; and
   determining an absorbance of the transmitted light by the gas component.

17. The method of claim 16, wherein transmitting includes transmitting light having a broad or narrow wavelength band through a narrow band pass filter, wherein said narrow pass band filter allows a majority of light in said known wavelength band to pass.

18. The method of claim 14, wherein the measurements of T1, T2 and P occur within about 0.2 seconds or less of each other.

19. The method of claim 14, wherein the measurements of T1, T2 and P are taken at a rate of about 10 Hz or faster.

20. The method of claim 14, wherein the components of the gas include $CO_2$ and $H_2O$, and wherein the gas is air.

21. The method of claim 14, wherein determining the dry mole fraction includes correcting for a delay due to spatial separation in temperature signals received from the inlet port and the outlet port, wherein the delay is a function of a flow rate of the gas in the flow cell.

22. The method of claim 14, wherein the measured pressure P is one of a mean pressure or a differential pressure.

23. A gas analysis system that measures dry mole fraction of components of a gas, the system comprising:
   a flow cell within which a gas is flowed from an inlet port to an outlet port;
   a light source configured to transmit light through the flow cell;
   a detector subsystem configured to output an absorbance signal representing an absorbance of light by the components of the gas in the flow cell;
   a first temperature sensor positioned proximal to the input port of the'e flow cell;
   a second temperature sensor positioned proximal to the output port of the flow cell;
   a pressure sensor adapted to measure pressure at an interior point of the flow cell; and
   an intelligence module coupled with the first and second temperature sensors, the pressure sensor, and with the detector subsystem, the intelligence module adapted to determine a dry mole fraction of the components based on the absorbance signal and substantially simultaneous measurements of the pressure of the gas and of the temperature of the gas by the first and second temperature sensors, the substantially simultaneous measurements being taken at a rate of about 1.0 Hz or faster.

24. The system of claim 23, wherein the measurements of the pressure and of the temperature of the gas by the first and second temperature sensors occur within about 0.2 seconds or less of each other.

25. The system of claim 23, wherein the measurements of the pressure and of the temperature of the gas by the first and second temperature sensors are taken at a rate of about 10 Hz or faster.

26. The system of claim 23, wherein the components of the gas include $CO_2$ and $H_2O$, and wherein the gas, is air.

27. The system of claim 23, wherein the flow cell is removably attached to a structure between the light source and detector subsystem.

28. The system of claim 23, wherein the intelligence module is further adapted to correct for a delay due to spatial separation in the temperature signals received from the first and second temperature sensors, wherein the delay is a function of a flow rate of the gas in the flow cell.

29. The system of claim 23, further including a thermal insulation sleeve configured to insulate at least a portion of the flow cell from other components of the system.

30. The system of claim 23, wherein each of the first and second temperature sensors includes a thermocouple positioned at a central point of a flow path defined by the respective port.

31. A removable gas cell adapted to be disposed between light source and detector sections of a gas analyzer system, the removable gas cell including:
   a housing structure defining a gas flow channel;
   a first opening at one end of the gas flow channel;
   a second opening at the other end of the gas flow channel, wherein the first and second openings define a light path along which light from a light source passes through the cell to the detector section; and
   a gas inlet port;
   a gas outlet port, wherein the inlet and outlet ports are located on the housing structure off of the optical axis;
   a first temperature sensor located proximal to the inlet port and adapted to measure a temperature of gas within the flow channel proximal to the inlet port at a rate of about 1.0 Hz or faster; and
   a second temperature sensor located proximal to the outlet port and adapted to measure a temperature of gas within the flow channel proximal to the outlet port at a rate of about 1.0 Hz or faster.

32. The removable gas cell of claim 31, further including a pressure sensor located at an interior point of the housing structure in the gas flow channel, the pressure sensor adapted to measure a pressure of a gas at an interior point in the flow cell.

33. The removable gas cell of claim 31, wherein at least one of the first and second temperature sensors includes a thermocouple positioned at a central point of a flow path defined by the respective port.

34. The removable gas cell of claim 31, further including a gas intake tube, coupling the atmosphere with the input port, the intake tube having a length of less than about 1.0 meters.

35. A removable gas cell adapted to be disposed between light source and detector sections of a gas analyzer system, the removable gas cell including:
   a housing structure defining a gas flow channel;
   a first opening at one end of the gas flow channel;
   a second opening at the other end of the gas flow channel, wherein the first and second openings define a light path along which light from a light source passes through the cell to the detector section;
   a gas inlet port;
   a gas outlet port, wherein the inlet and outlet ports are located on the housing structure off of the optical axis;
   a first temperature sensor adapted to measure a temperature of a gas flowing in the flow channel at a rate of about 1.0 Hz or faster; and
   a pressure sensor adapted to measure a pressure of the gas at an interior point in the flow cell at a rate of about 1.0 Hz or faster.

36. The removable gas cell of claim 35, further including a second temperature sensor located proximal to the outlet port, wherein the first temperature sensor is located proximal to the input port.

37. The removable gas cell of claim 36, wherein at least one of the first and second temperature sensors includes a thermocouple positioned at a central point of a flow path defined by the respective port.

38. The removable gas cell of claim 35, further including a gas intake tube, coupling the atmosphere with the input port, the intake tube having a length of less than about 1.0 meters.

39. A gas analyzer, comprising:
   a) a detector section including a detector;
   b) a source section including a light source;
   c) a first optical window coupled with the detector section;
   d) a second optical window coupled with the source section; and
   e) a removable gas cell removably disposed between the source and detector sections, the removable gas cell including:
   a housing structure defining a gas flow channel, wherein the light from the light source passes through the gas flow channel to the detector section along a light path;
   a gas inlet port;
   a gas outlet port, wherein the inlet and outlet ports are located on the housing structure;
   a first temperature sensor adapted to measure a temperature of gas flowing in the flow channel; and
   a pressure sensor adapted to measure a pressure of the gas, wherein the first and second optical windows provide an airtight seal for components within the source and detector sections.

40. The gas analyzer of claim 39, wherein the pressure sensor is adapted to measure the pressure at an interior point in the flow cell.

41. The gas analyzer of claim 40, wherein the pressure sensor is located at an interior point in the flow cell.

* * * * *